United States Patent [19]

Menard et al.

[11] Patent Number: 4,723,051

[45] Date of Patent: Feb. 2, 1988

[54] XYLENE ISOMERIZATION PROCESS

[75] Inventors: Kevin P. Menard; James R. Butler, both of Big Spring, Tex.

[73] Assignee: Cosden Technology, Inc., Dallas, Tex.

[21] Appl. No.: 903,382

[22] Filed: Sep. 3, 1986

Related U.S. Application Data

[63] Continuation-in-part of Ser. No. 826,848, Feb. 6, 1986, Pat. No. 4,665,258.

[51] Int. Cl.$^4$ .............................................. C07C 5/22
[52] U.S. Cl. .................................................... 585/481
[58] Field of Search ......................................... 585/481

[56] References Cited

U.S. PATENT DOCUMENTS

| | | |
|---|---|---|
| 3,436,174 | 4/1969 | Sand . |
| 3,476,821 | 11/1969 | Brandenburg et al. . |
| 3,480,539 | 11/1969 | Voorhies et al. . |
| 3,677,973 | 7/1972 | Mitsche et al. . |
| 3,723,552 | 3/1973 | Mitsche et al. .................... 585/481 |
| 3,780,122 | 12/1973 | Pollitzer . |
| 3,915,895 | 10/1975 | Suggitt et al. . |
| 4,120,908 | 10/1978 | Kamiyama et al. . |
| 4,128,591 | 12/1978 | Carr et al. . |

OTHER PUBLICATIONS

"Xylenes and Ethylbenzene," Kirk-Othmer, *Encyclopedia of Chemical Technology*, Third Edition, John Wiley & Sons, 1984, vol. 24, pp. 709-744.

"Molecular Sieves," Kirk-Othmer, *Encyclopedia of Chemical Technology*, Third Edition, John Wiley & Sons, 1984, vol. 15, pp. 638-643.

*Primary Examiner*—Curtis R. Davis
*Attorney, Agent, or Firm*—William D. Jackson; John K. Abokhair; M. Norwood Cheairs

[57] ABSTRACT

Process for the isomerization of xylene feedstock employing an aluminum-deficient mordenite catalyst. The xylene feedstock is passed into a reaction zone and in contact with a mordenite catalyst having a silica/alumina mole ratio of at least 30. The xylene feedstock may comprise a substantially pure meta-xylene, a mixture of xylene isomers, or in the preferred embodiment, a mixture of xylene isomers and ethylbenzene in which para-xylene is present in less than an equilibrium amount, and ethylbenzene present in an amount greater than the para-xylene content. The reaction zone is operated at a temperature within the range of 350°-600° C. and a hydrogen pressure within the range of 200-1000 psig to effect isomerization of xylene isomers to provide an increased para-xylene content and disproportionation of ethylbenzene to provide a reduced ethylbenzene content in the product.

18 Claims, No Drawings

XYLENE ISOMERIZATION PROCESS

This application is a continuation-in-part of application Ser. No. 826,848 filed Feb. 6, 1986, now U.S. Pat. No. 4,665,258, entitled "Toluene Disproportionation Process."

TECHNICAL FIELD

This invention relates to xylene isomerization and more particularly to xylene isomerization with co-disproportionation of ethylbenzene employing mordenite catalysts of low aluminum content.

ART BACKGROUND

The isomerization of xylene feedstocks is a conventional procedure in petroleum refining operations. Most such feedstocks contain the isomers ortho-, meta-, and para-xylene, and ethylbenzene together with small quantities of other aromatic compounds and saturated hydrocarbons. Xylene isomerization normally is carried out as an intermediate function in a so-called "xylene loop" in which a desired xylene isomer (usually para-xylene but in some cases also ortho-xylene) is withdrawn from a mixture of the isomers found in a process stream such as the output from a reforming unit. The remainder of the process stream is used as a feed stock for the isomerization unit. The output from the isomerization unit is recycled and mixed with fresh charge to the xylene loop.

While ortho-xylene can be separated from the other xylene isomers and ethylbenzene by fractional distillation, para-xylene which has a boiling point about 1° C. below meta-xylene and about 2° C. above ethylbenzene, is normally separated in the xylene loop by crystallization or selective adsorption. Typically, the para-xylene content is reduced by the crystallization or selective adsorption step to less than 10 and preferably less than 5 weight percent. The feedstream with the para-xylene thus extracted is applied to the isomerization reactor where isomerization of the ortho- and meta-xylenes results in a product in which the para-xylene is at approximately equilibrium concentration. The procedures and reactions involved in xylene isomerization are described in greater detail in Kirk-Othmer, *Encyclopedia or Chemical Technology*, Third Edition, John Wiley & Sons 1984, "Xylenes and Ethylbenzene," Vol. 24, pages 709–744, to which reference is made for a more complete description of this process.

Mordenite catalyst have been proposed for use in the isomerization of xylene feedstocks as well as in various other hydrocarbon processing operations. Mordenite is a crystalline aluminosilicate zeolite having a network of silicon and aluminum atoms interlinked in its crystalline structure through oxygen atoms. For a general description of mordenite catalysts, reference is made to Kirk-Othmer, *Encyclopedia of Chemical Technology*, 3rd Edition, "Molecular Sieves", Vol. 15, pages 638–643. Mordenite as found in nature or as synthesized, typically has a relatively low silica to alumina mole ratio of about 10 or less. Such conventionally structured mordenite catalysts are commonly employed in transalkylation processes such as the disproportionation of toluene. In addition, mordenite catalysts having a substantially reduced alumina content are employed in the disproportionation of toluene, and mordenite catalysts of moderately reduced alumina content have been proposed for use in the isomerization of xylene feedstocks.

Perhaps the widest use of mordenite catalysts in hydrocarbon conversion processes has been in the disproportionation of toluene feedstocks. Natural or synthetic mordenite having a silica/alumina mole ratio of about 10 may be used for this purpose. In addition, so-called alumina deficient mordenites, catalysts having a silica/alumina ratio greater than 10 and sometimes ranging up to 100, may also be used in the disproportionation of toluene as well as in various other hydrocarbon conversion processes. Low aluminum mordenites may be prepared by direct synthesis as disclosed for example in U.S. Pat. No. 3,436,174 to Sand or by acid extraction of a more conventionally prepared mordenite as disclosed in U.S. Pat. No. 3,480,539 to Voorhies et al.

In processes involving the transalkylation of aromatic compounds and specifically the disproportionation of aromatic feedstreams, the prior art indicates that the silica/alumina ratio has a bearing upon the reaction temperatures which should be employed. Specifically in the case of toluene disproportionation, the prior art indicates that while relatively high temperatures can be employed for high aluminum mordenites (low silica/alumina ratios), somewhat lower temperatures should be employed for low aluminum mordenites. This is reflected by a consideration of U.S. Pat. Nos. 3,780,122 (Pollitzer), 3,677,973 (Mitsche et al), and 3,476,821 (Brandenburg et al), which when considered together, disclose experimental work carried out for mordenites of silica/alumina ratios ranging from 10 to 97.

The patent to Pollitzer discloses the transalkylation of toluene using a mordenite catalyst having a silica/alumina ratio up to about 100 and preferably at least about 15 which is obtained by acid extraction of a mordenite zeolite having a silica/alumina ratio of less than 10. The transalkylation conditions include a temperature within the range from about 200° C. to about 480° C. and a pressure ranging from about atmospheric to about 100 atmospheres. Specifically disclosed are catalysts A and B having silica to alumina ratios of about 15.5 and about 10.7, respectively. These catalysts were employed in Example II of Pollitzer in toluene transalkylation tests which were run for durations slightly in excess of seven days. The lower ratio catalyst B was run at a temperature starting at 300° C. which was progressively increased over the life of the test to 400° C. For the higher ratio catalyst A, the temperature range was somewhat lower. It ranged from an initial value of 299° C. to a final value of 374° C.

While the higher ratio catalyst showed a somewhat greater activity than the other, neither catalyst showed good aging tolerance. Both lost about 15% activity in the first four days with some increase in activity occurring after that time. Whether the increase after the initial decrease in activity was due to an "edge" effect of the catalysts or because of the progressively increasing temperature conditions cannot be determined because of the short duration of the test. The yield in the Pollitzer process is severely affected by water in the toluene feed stock. As shown in Table II, even a very small amount of water (15 ppm) reduces toluene conversion substantially.

In the patent to Mitsche et al, the reaction conditions are said to include a temperature ranging from 200° C. to about 480° C. and a pressure of about 1 atmospheric to 1500 psig. The catalyst employed includes about 60–90 weight percent low alumina mordenite composited with an alumina sol to provide a silica alumina ratio of the composite catalyst from about 10 to about 30. The specifically disclosed composite catalyst in Example I is 50% mordenite having a silica/alumina mole ratio of 19.7 and 42% alumina (to provide an overall silica/alumina ratio of about 10.7). This composite catalyst was employed in the transalkylation of toluene at reaction conditions of 420° C. and 500 psig.

As noted previously, when mordenites of higher silica/alumina ratios are used in the transalkylation of alkylaromatics, the practice has been to use lower temperatures. It is also common in this case to promote the catalyst with a catalytically active metallic content. Thus, the aforementioned patent to Brandenburg et al discloses disproportionation reactions employing mordenite catalysts having a silica/alumina ratio within the range of 10-100 and preferably within the range of about 20-60. Here the desired temperature ranges are said to be from about 400°-750° F. and preferably 450°-640° F. Metal promoters were found to substantially increase activity and catalyst life. Without the addition of a metal promoter, the optimum silica/alumina ratio in terms of activity appears to be about 24 in tests run at 550° F., as reported in Example I. In Example III, a "product ratio" is presented as an indication of catalyst life. Mordenite having a silica/alumina mole ratio of 52 promoted with 5.2 weight percent nickel sulfide was shown to have a product ratio slightly less than that for mordenite of a silica/alumina mole ratio of 24 when promoted with 0.4 weight percent platinum sulfide. Example V discloses comparative disproportionation runs carried out with mordenite of a silica/alumina mole ratio of 24:1 at temperatures of 550°-575° F. In run 1 with no added metal, catalyst activity decreased rapidly even under the mild disproportionation conditions employed. In runs 2 and 3, five weight percent nickel sufide was added to the catalyst and catalytic activity was extended although the tests were run for only a limited time (no more than 48 hours).

The use of mordenite catalysts of high silica/alumina ratio in the disproportionation and isomerization of alkylaromatic compounds is also disclosed in U.S. Pat. No. 3,915,895 to Suggitt et al. The silica/alumina mole ratios proposed in Suggitt range from 10 to about 100 (preferably 12-80 and more preferably about 25 to 50). The catalysts for which experimental information is given in Suggitt had silica/alumina ratios of 18 and 39. In the disproportionation of toluene at the conditions employed (550° F. and 200 or 800 psig.), neither catalyst showed particularly good activity although the higher alumina catalyst promoted with silver was better than the unpromoted catalyst. A similar alumina deficient mordenite promoted with copper and chromium was evaluated for the disproportionation of ortho-xylene as well as toluene. The ortho-xylene feedstock was applied to the catalyst at a hydrogen pressure of 800 psig and at temperatures ranging from 550°-625° F. The experimental results reported in Table II of Suggitt indicate that disproportionation of toluene and trimethylbenzene occurred along with isomerization of the ortho-xylene to the para- and meta-isomers. The test results reported in Table II indicate that maximum isomerization occurred within the lower portion of the 550°-625° F. temperate range whereas disproportionation, as indicated by toluene and trimethylbenzene yield, increased progressively with temperature.

The use of mordenite catalysts of reduced alumina content in the isomerization of xylene feedstreams containing a mixture of xylene isomers and ethylbenzene is disclosed in U.S. Pat. Nos. 4,120,908 to Kamiyama et al and 4,128,591 to Carr et al. These patents indicate that in terms of both ethylbenzene conversion and xylene isomerization, mordenite catalysts of only moderately diminished alumina content should be employed. Thus, the patent to Kamiyama et al discloses the isomerization of xylenes at temperatures of 180°-250° C. using an acid-leched mordenite catalyst having a silica/alumina ratio within the range of 15-21. The experimental data in Kamiyama indicate that maximum xylene isomerization and ethylbenzene conversion occur at a silica/alumina ratio of about 17-21 with much poorer results obtained when the silica/alumina ratio is increased up to about 23-29.

The patent to Carr et al indicates that at a higher reaction temperature, 427° C., the silica/alumina ratio should be greater than 9:1 to 11:1 but less than 17:1. At this higher temperature, a mordenite having a silica/alumina ratio of 17, identified in the patent as catalyst G, was found to be "clearly unacceptable."

SUMMARY OF THE INVENTION

In accordance with the present invention, there is provided a new and improved process for the isomerization of a xylene feedstock to produce a product having an enhanced para-xylene content. In carrying out the invention, a xylene feedstock containing meta-xylene is passed into a reaction zone containing an aluminum deficient mordenite catalyst having a silica/alumina mole ratio of at least 30. Preferably the catalyst has a silica/alumina ratio within the range of 40-60. Hydrogen co-feed is also supplied to the reaction zone. The reaction zone is operated at a temperature within the range of 350°-600° C. and a hydrogen pressure within the range of 200-1000 psig to effect isomerization of the xylene feedstock to provide a product of an increased paraxylene content and reduced meta xylene content.

In a further aspect of the invention, there is provided a process for the isomerization of a xylene feedstock to produce a product having an enhanced para-xylene content, while at the same time having a reduced ethylbenzene content. In this embodiment of the invention, a xylene feedstock containing a mixture of xylene isomers and ethylbenzene in which the para-xylene content is less than equilibrium and the ethylbenzene content greater than the para-xylene concentration is passed into a reaction zone and in contact with an aluminum-deficient mordenite catalyst as described above. The reaction zone is operated at the aforementioned temperature and pressure conditions to effect isomerization of the xylene isomers to produce a product of increased para-xylene content and reduced ethylbenzene content. The resulting product of increased para-xylene content and diminished ethylbenzene content is withdrawn from the reaction zone.

Preferred reaction conditions include a temperature within the range of 400°-440° C. and a hydrogen pressure of about 300-600 psig. A preferred catalyst for use in the invention is hydrogen mordenite having a silica/alumina ratio of about 48. In a further embodiment of the invention, a preflush gas is supplied to the reaction zone prior to initiating the isomerization reaction. The preflush gas is heated to a temperature sufficient to strip water from the catalyst so that a substantially dehydrated catalyst is arrived at when the xylene feed is started.

DETAILED DESCRIPTION

As indicated by the aforementioned material in Kirk-Othmer, Vol. 24, at page 729, the thermodynamic equilibrium concentrations of $C_8$ aromatic isomers vary as a function of temperature. As the temperature increases, the equilibrium concentrations for ortho-xylene and ethylbenzene increase while the equilibrium concentrations for meta-xylene and paraxylene decrease, the latter at a much lower rate than the former. The reactions encountered in the isomerization of a xylene feedstream involve xylene isomerization, and transalkylation of ethylbenzene and xylenes. The xylene isomerization reaction may be characterized as involving the reaction of about three moles of meta-xylene and one mole of orthoxylene to produce the equilibrium mixture of the three xylene isomers which is roughly two moles of meta-xylene to one mole each of ortho-and paraxylene. The ethylbenzene alkylation reactions include disporportionation of ethylbenzene to benzene and diethylbenzene and a reaction of ethylbenzene with xylene to produce benzene and ethyldimethylbenzene. The xylene transalkylation reactions include disporportionation of xylene to toluene and trimethylbenzenes and reaction of xylene with ethylbenzene to produce toluene and ethyltoluene.

Based upon the foregoing analysis, it will be recognized that the amount of toluene in the product stream from a xylene isomerization reactor can be used as a measure of xylene loss through xylene disproportionation whereas the amount of benzene in the product stream can be used to indicate the amount of ethylbenzene disproportionation. The quantity of dimethylethylbenzene in the product in turn provides a measure of the amount of xylene lost in the ethylbenzene disporportionation.

In the present invention, xylene isomerization to produce a product of enhanced para-xylene content is carried out employing an aluminum-deficient mordenite catalyst. The xylene feedstock may vary from substantially pure meta-xylene or a mixture of xylene isomers to a mixture of xylene isomers and ethylbenzene as commonly found in a typical xylene loop. In this embodiment of the invention, the para-xylene is present in less than an equilibrium amount and the ethylbenzene is present in a concentration greater than the para-xylene concentration. There is a distinct advantage in terms of aging quality of using aluminum deficient mordenites as catalysts in the transalkylation of alkylaromatic compounds. As disclosed in parent application Ser. No. 826,848, aging quality progressively increases as aluminum content decreases. Thus, in the parent application aging tests were carried out for mordenites having silica/alumina ratios ranging from 10 to 18 to 48. At a silica/alumina ratio of 18, a moderate increase in aging quality was observed and at a silica/alumina ratio of 48, a very pronounced increased in aging quality was observed with only a slight loss in activity. As also disclosed in application Ser. No. 826,848, toluene disporportionation over an alumina deficient mordenite catalyst was effective at substantially higher temperatures than those indicated by the prior art.

The considerations described above are applicable in the present invention involving the isomerization of xylene feedstocks. Specifically, an aluminum deficient mordenite catalyst having a silica/alumina ratio of at least 30, and preferably within the range of 40-60, is employed in the isomerization of a xylene feedstock containing ethylbenzene at temperatures well above those indicated as acceptable by the prior art. The mordenite catalyst employed in the present invention is disclosed in parent application Ser. No. 826,848 and for a more detailed description of such mordenite catalysts and their aging and temperature tolerance characteristics, reference is made to application Ser. No. 826,848, the entire disclosure of which is incorporated herein by reference.

In experimental work carried out respecting the invention, a mordenite catalyst having a silica/alumina ratio of 48 (described in application Ser. No. 826,848 as catalyst "C") was employed in the isomerization of hydrocarbon mixtures extracted from the feed stream to a commercial xylene isomerization unit. The commercial unit had a design capacity of about 31,000 barrels per day and was operated at nominal temperature and pressure conditions of about 318° C. and 250 psig.

A ZSM-5 type catalyst was employed in the commercial isomerization unit. While the exact nature of the catalyst is not available, based upon published data (Kirk-Othmer, Vol. 24, pp. 732–733), the zeolite was presumably in the NiHZSM-5 form. The xylene feedstream was supplied to the reactor to provide a space velocity (WHSV) of 7 and hydrogen cofeed was supplied to provide a ratio of hydrogen to hydrocarbons of 4.5.

A typical analysis of the xylene feedstream and the effluent product for the commercial unit are set forth below in Table I. As shown, the commercial catalyst functions to convert the xylene feedstream which is rich in ortho-and meta-isomers into an approximately equilibrium concentration of para-, meta-, and ortho-xylene. In addition, about 20% by weight of the ethylbenzene in the feedstream is disproportionated to benzene and $C_9+$ aromatic hydrocarbons.

TABLE I

| | Feed | Effluent |
|---|---|---|
| Non-Aromatics | 0 | 1.1 |
| Benzene | 0.1 | 1.9 |
| Toluene | 0.2 | 1.0 |
| Ethylbenzene | 18.6 | 15.8 |
| Paraxylene | 2.5 | 18.1 |
| Metaxylene | 53.7 | 40.9 |
| Orthoxylene | 24.6 | 16.8 |
| $C_9+$ | 0.4 | 4.4 |

The mordenite catalyst was run for a period of 7 days. At the conclusion of this period it was regenerated by passing a mixture of 90% nitrogen and 10% air over the catalyst at a temperature of 400° C. and a pressure of 70 psig for a period of 24 hours. After regeneration and further shutdown for about 12 days to effect repairs to the test system, the catalyst was used further in the isomerization of a feed stream for a period of about 12 days. During the test procedure for both the fresh and regenerated catalyst the reaction temperature in the reaction vessel varied from about 200° to about 475° C. and the pressure ranged from about 200 to about 600 psig. The hydrocarbon velocity across the catalyst bed ranged from about 1 to 12 LHSV (1.4 to 16.7 WHSV). Hydrogen was co-fed along with the xylene feed stream at rates to provide a hydrogen/hydrocarbon (the composite of the xylene and ethylbenzene content of the feed stream) ratio within the range of about 2 to about 5. In a few cases the isomerization reactor was run without a hydrogen cofeed.

Two similar feedstreams were used in the course of the experimental work. The first, identified herein as Feed #1, was used during the first seven days. The second (Feed #2) was used for the remainder of the experimental work carried out after regeneration of the catalyst. The compositions of the two feedstreams in wt. % are set forth below in Table II:

TABLE II

|  | Feed #1 | Feed #2 |
|---|---|---|
| Non-Aromatics | 0 | 0.3 |
| Benzene | 0.1 | 0 |
| Toluene | 0.2 | 0.4 |
| Ethylbenzene | 18.7 | 19.4 |
| Paraxylene | 2.5 | 2.5 |
| Metaxylene | 54.1 | 54.1 |
| Orthoxylene | 24.8 | 22.8 |
| $C_9+$ | 0.4 | 0.8 |

In the course of the experimental varying conditions of pressure, temperature, space velocity, and hydrogen/hydrocarbon (ethylbenzene + xylene) mole ratio were employed in the experimental runs as indicated by a statistically designed experimental program. The results of this experimental work are reported on a sample-by-sample basis in Tables III–VI. In these tables, the experimental data reported is identified to the left of each table. The data is reported in successive columns arranged by run number and samples taken within each run. Thus, Run 1 involved the analysis of six product samples identified therein as samples 1.1 through 1.6. Other runs, e.g. Runs 12 and 13, involved the analysis of only one sample. The experimental data sent forth in Tables III–VI is presented in summary form for each run in Table VII. In Table VII, the test data for each of Runs 1–13 represent an average of the results for the samples taken during the run.

TABLE III

| EXPERIMENT | 1 | | | | | | 2 | | | 2B | 3 | |
|---|---|---|---|---|---|---|---|---|---|---|---|---|
| SAMPLE NUMBER | 1.1 | 1.2 | 1.3 | 1.4 | 1.5 | 1.6 | 2.1 | 2.2 | 2.3 | 2B.1 | 3.1 | 3.2 |
| AGE OF CATALYST IN DAYS | 0.0 | 0.5 | 0.8 | 1.1 | 1.6 | 2.1 | 2.2 | 2.6 | 2.8 | 3.0 | 3.2 | 3.4 |
| AVG. BATH TEMP. | 470 | 470 | 470 | 470 | 473 | 475 | 303 | 303 | 303 | 351 | 220 | 201 |
| PRESSURE (PSIG) | 600 | 600 | 600 | 600 | 600 | 600 | 250 | 250 | 250 | 250 | 200 | 200 |
| LIQUID ANALYSIS WT % | | | | | | | | | | | | |
| NON-AROM | 0.9 | 0.3 | 0.3 | 0.4 | 0.6 | 0.6 | 0.0 | 0.0 | 0.0 | 0.0 | 0.2 | 0.2 |
| BZ | 5.3 | 5.7 | 5.5 | 5.3 | 6.8 | 6.7 | 0.1 | 0.0 | 0.0 | 0.1 | | |
| TOL | 21.1 | 24.1 | 22.9 | 21.3 | 27.8 | 27.5 | 0.2 | 0.1 | 0.1 | 0.1 | 0.2 | 0.2 |
| EB | 4.4 | 3.2 | 3.7 | 4.7 | 1.9 | 1.9 | 18.7 | 18.8 | 18.8 | 18.8 | 18.8 | 18.8 |
| P-XYL | 9.9 | 9.7 | 9.8 | 10.4 | 9.0 | 8.9 | | | | 1.8 | | |
| O-XYL | 10.9 | 9.9 | 10.0 | 10.5 | 9.3 | 9.3 | 24.6 | 24.6 | 24.6 | 24.6 | 24.1 | 24.4 |
| M-XYL | 23.9 | 22.0 | 22.4 | 23.6 | 20.8 | 20.7 | 56.0 | 56.1 | 56.1 | 54.4 | 56.4 | 55.8 |
| C9+ | 5.5 | 5.3 | 5.6 | 5.3 | 4.5 | 4.9 | 0.4 | 0.1 | 0.1 | 0.0 | 0.2 | 0.6 |
| M-ET | 2.3 | 2.5 | 2.7 | 2.8 | 1.8 | 1.8 | | | | | | |
| P-ET | 1.2 | 1.3 | 1.5 | 1.5 | 0.9 | 1.0 | | | | | | |
| O-ET | 0.6 | 0.7 | 0.7 | 0.1 | 0.5 | 0.5 | | | | | | |
| 1,3,5-TMB | 3.5 | 3.8 | 3.7 | 3.4 | 4.0 | 4.1 | | | | | | |
| 1,2,4-TMB | 9.1 | 10.0 | 9.7 | 8.8 | 10.5 | 10.5 | | | | | | |
| 1,2,3-TMB | 1.4 | 1.5 | 1.5 | 1.3 | 1.6 | 1.6 | | | | | | |
| EB RATE (MOLES/MIN) | 0.00075 | 0.00075 | 0.00075 | 0.00075 | 0.00075 | 0.00075 | 0.00489 | 0.00505 | 0.00505 | 0.00505 | 0.00038 | 0.00038 |
| XYL RATE (MOLES/MIN) | 0.00328 | 0.00328 | 0.00328 | 0.00328 | 0.00328 | 0.00328 | 0.02131 | 0.02196 | 0.02196 | 0.02196 | 0.00164 | 0.00164 |
| H2 RATE (MOLES/MIN) | 0.01884 | 0.01884 | 0.01884 | 0.01884 | 0.01884 | 0.01884 | 0.11830 | 0.11830 | 0.11830 | 0.11830 | 0.00000 | 0.00000 |
| H2/HC MOLAR RATIO | 4.640 | 4.640 | 4.640 | 4.640 | 4.640 | 4.640 | 4.483 | 4.349 | 4.349 | 4.349 | 0.000 | 0.000 |
| LHSV | 2.00 | 2.00 | 2.00 | 2.00 | 2.00 | 2.00 | 13.00 | 13.40 | 13.40 | 13.40 | 1.00 | 1.00 |
| WHSV | 2.78 | 2.78 | 2.78 | 2.78 | 2.78 | 2.78 | 18.09 | 18.65 | 18.65 | 18.65 | 1.39 | 1.39 |
| XYLENE CONVERSION | | | | | | | | | | | | |
| M-XYLENE CONV. | 30.2 | 32.4 | 32.5 | 30.4 | 34.4 | 33.4 | −1.9 | −1.9 | −2.1 | −0.4 | −2.4 | −1.7 |
| O-XYLENE CONV. | 13.9 | 15.0 | 15.2 | 14.2 | 16.0 | 15.5 | 0.2 | 0.2 | 0.2 | 0.1 | 0.7 | 0.4 |
| P-XYLENE PRODUCTION | 7.4 | 7.1 | 6.9 | 8.0 | 6.0 | 6.4 | −2.5 | −2.5 | −2.5 | −0.7 | −2.5 | −2.5 |
| XYLENE CONSUMPTION | | | | | | | | | | | | |
| % XYLENES RECOV. | 54.9 | 51.1 | 51.8 | 54.7 | 48.0 | 47.8 | 99.0 | 99.1 | 99.1 | 99.3 | 98.9 | 98.5 |
| TOLUENE YIELD (WT %) | 20.9 | 23.5 | 21.8 | 21.2 | 26.1 | 27.3 | 0.0 | −0.1 | −0.1 | −0.1 | 0.0 | 0.0 |
| ETHYLBENZENE DISPROPORT. | | | | | | | | | | | | |
| % EB CONSUMED | 76.5 | 83.1 | 81.0 | 74.7 | 90.4 | 89.8 | 0.0 | −0.4 | −0.7 | −0.8 | −0.6 | −0.5 |
| BENZENE YIELD (WT %) | 5.2 | 5.5 | 5.9 | 5.2 | 8.9 | 6.6 | 0.0 | 0.3 | −0.1 | 0.0 | −0.1 | −0.1 |
| HEAVIES YIELD (WT %) | 23.2 | 24.4 | 24.1 | 23.0 | 22.1 | 24.0 | 0.0 | −0.2 | −0.2 | −0.4 | −0.2 | 0.2 |

TABLE IV

| EXPERIMENT | | 4 | | | 4B | 5 | | | 6 | | | 1 |
|---|---|---|---|---|---|---|---|---|---|---|---|---|
| SAMPLE NUMBER | 3.3 | 4.1 | 4.2 | 4.3 | 4B.1 | 5.1 | 5.2 | 5.3 | 6.1 | 6.2 | 6.3 | 7.1 |
| AGE OF CATALYST IN DAYS | 4.0 | 4.3 | 4.6 | 5.0 | 5.2 | 5.5 | 5.7 | 6.0 | 6.2 | 6.4 | 7.0 | 0.0 |
| AVG. BATH TEMP. | 202 | 452 | 452 | 452 | 401 | 451 | 451 | 451 | 353 | 353 | 353 | 468 |
| PRESSURE (PSIG) | 200 | 200 | 200 | 200 | 200 | 200 | 200 | 200 | 610 | 610 | 610 | 600 |
| LIQUID ANALYSIS WT % | | | | | | | | | | | | |
| NON-AROM | 0.3 | 0.4 | 0.1 | 0.3 | 0.3 | 0.2 | 0.1 | 0.1 | 0.2 | 0.3 | 0.1 | 0.9 |
| BZ | | 3.4 | 3.8 | 3.8 | 3.4 | 0.7 | 0.3 | 0.1 | 0.1 | 0.1 | | 6.8 |
| TOL | 0.2 | 12.9 | 14.4 | 14.4 | 12.8 | 2.2 | 0.5 | 0.2 | 0.3 | 0.3 | | 28.2 |
| EB | 18.8 | 9.2 | 8.0 | 8.1 | 9.1 | 17.0 | 18.5 | 19.0 | 18.7 | 18.8 | 19.1 | 1.9 |
| P-XYL | | 10.5 | 12.9 | 13.3 | 14.1 | | | 3.1 | 3.3 | 2.6 | 2.6 | 8.6 |
| O-XYL | 24.4 | 15.5 | 13.3 | 13.0 | 13.5 | 21.9 | 23.6 | 24.1 | 24.2 | 24.2 | 23.9 | 8.9 |

TABLE IV-continued

| EXPERIMENT | | 4 | | | 4B | 5 | | | 6 | | | 1 |
|---|---|---|---|---|---|---|---|---|---|---|---|---|
| SAMPLE NUMBER | 3.3 | 4.1 | 4.2 | 4.3 | 4B.1 | 5.1 | 5.2 | 5.3 | 6.1 | 6.2 | 6.3 | 7.1 |
| M-XYL | 55.8 | 32.9 | 29.3 | 29.8 | 29.9 | 55.2 | 56.4 | 53.2 | 52.7 | 53.4 | 53.9 | 19.8 |
| C9+ | 0.5 | 3.5 | 4.3 | 4.1 | 4.0 | 0.7 | 0.6 | 0.2 | 0.6 | 0.3 | 0.4 | 5.5 |
| M-ET | | 1.9 | 2.4 | 2.5 | 2.3 | 0.4 | | | | | | 1.9 |
| P-ET | | 1.0 | 1.3 | 1.3 | 1.3 | 0.2 | | | | | | 1.0 |
| O-ET | | 0.5 | 0.6 | 0.7 | 0.6 | 0.1 | | | | | | 0.5 |
| 1,3,5-TMB | | 2.1 | 2.4 | 2.4 | 2.2 | 0.3 | | | | | | 4.0 |
| 1,2,4-TMB | | 5.4 | 6.3 | 6.3 | 5.7 | 1.0 | | | | | | 10.4 |
| 1,2,3-TMB | | 0.8 | 0.9 | 0.9 | 0.8 | 0.1 | | | | | | 1.6 |
| EB RATE (MOLES/MIN) | 0.00038 | 0.00038 | 0.00038 | 0.00038 | 0.00038 | 0.00523 | 0.00523 | 0.00523 | 0.00038 | 0.00038 | 0.00038 | 0.00075 |
| XYL RATE (MOLES/MIN) | 0.00164 | 0.00164 | 0.00164 | 0.00164 | 0.00164 | 0.02275 | 0.02275 | 0.02275 | 0.00164 | 0.00164 | 0.00164 | 0.00328 |
| H2 RATE (MOLES/MIN) | 0.00000 | 0.01205 | 0.01205 | 0.01205 | 0.01205 | 0.00000 | 0.00000 | 0.00000 | 0.00000 | 0.00000 | 0.00000 | 0.01652 |
| H2/HC MOLAR RATIO | 0.000 | 5.937 | 5.937 | 5.937 | 5.937 | 0.000 | 0.000 | 0.000 | 0.000 | 0.000 | 0.000 | 4.068 |
| LHSV | 1.00 | 1.00 | 1.00 | 1.00 | 1.00 | 13.88 | 13.88 | 13.88 | 1.00 | 1.00 | 1.00 | 2.00 |
| WHSV | 1.39 | 1.39 | 1.39 | 1.39 | 1.39 | 19.32 | 19.32 | 19.32 | 1.39 | 1.39 | 1.39 | 2.78 |
| XYLENE CONVERSION | | | | | | | | | | | | |
| M-XYLENE CONV. | −1.7 | 21.2 | 24.8 | 24.6 | 24.2 | −1.1 | −2.3 | 0.9 | 1.5 | 0.7 | 0.2 | 34.3 |
| O-XYLENE CONV. | 0.4 | 9.3 | 11.5 | 11.9 | 11.3 | 2.9 | 1.2 | 0.7 | 0.6 | 0.6 | 0.9 | 15.9 |
| P-XYLENE PRODUCTION | −2.5 | 8.0 | 10.4 | 10.7 | 11.6 | −2.5 | −2.5 | 0.6 | 0.8 | 0.1 | 0.1 | 6.1 |
| XYLENE CONSUMPTION | | | | | | | | | | | | |
| % XYLENES RECOV. | 98.5 | 72.4 | 68.2 | 68.9 | 70.6 | 94.7 | 98.3 | 98.8 | 98.5 | 98.5 | 98.8 | 45.8 |
| TOLUENE YIELD (WT %) | 0.0 | 12.7 | 14.2 | 14.0 | 12.6 | 2.0 | 0.3 | 0.0 | 0.1 | 0.1 | −0.2 | 28.0 |
| ETHYLBENZENE DISPROPORT. | | | | | | | | | | | | |
| % EB CONSUMED | −0.5 | 50.8 | 57.2 | 57.2 | 51.3 | 9.1 | 1.1 | −1.6 | 0.1 | −0.5 | −2.1 | 89.8 |
| BENZENE YIELD (WT %) | −0.1 | 3.3 | 3.7 | 3.7 | 3.3 | 0.6 | 0.2 | 0.0 | 0.0 | 0.0 | −0.1 | 6.7 |
| HEAVIES YIELD (WT %) | 0.1 | 14.8 | 17.8 | 17.6 | 16.5 | 2.4 | 0.2 | −0.2 | 0.2 | −0.1 | 0.0 | 24.5 |

TABLE V

| EXPERIMENT | | | 8 | | | 9 | | | 8B | 8C | | 8D |
|---|---|---|---|---|---|---|---|---|---|---|---|---|
| SAMPLE NUMBER | 7.2 | 7.3 | 8.1 | 8.2 | 8.3 | 9.1 | 9.2 | 9.3 | 8B.1 | 8C.1 | 8C.2 | 8D.1 |
| AGE OF CATALYST IN DAYS | 0.5 | 1.0 | 2.0 | 2.2 | 3.0 | 3.1 | 3.2 | 3.3 | 3.4 | 3.5 | 3.6 | 3.8 |
| AVG. BATH TEMP. | 471 | 463 | 216 | 205 | 205 | 204 | 204 | 206 | 206 | 309 | 305 | 355 |
| PRESSURE (PSIG) | 600 | 600 | 600 | 600 | 600 | 600 | 600 | 600 | 600 | 600 | 600 | 600 |
| LIQUID ANALYSIS WT % | | | | | | | | | | | | |
| NON-AROM | 0.9 | 0.8 | 0.2 | 0.2 | 0.2 | 0.2 | 0.2 | 0.2 | 0.2 | 0.2 | 0.1 | 0.2 |
| BZ | 6.9 | 6.6 | 0.1 | 0.0 | 0.0 | 0.0 | 0.0 | 0.0 | 0.0 | 0.3 | 0.2 | 0.7 |
| TOL | 28.4 | 27.5 | 0.4 | 0.3 | 0.3 | 0.3 | 0.3 | 0.3 | 0.4 | 0.6 | 0.5 | 2.5 |
| EB | 1.8 | 2.2 | 20.8 | 18.5 | 21.3 | 21.1 | 19.1 | 19.1 | 21.3 | 18.6 | 18.8 | 16.2 |
| P-XYL | 8.6 | 8.8 | | 2.7 | | 0.8 | 2.7 | 2.7 | | 5.6 | 4.8 | 14.5 |
| O-XYL | 9.0 | 9.1 | 24.1 | 22.7 | 23.4 | 23.7 | 23.3 | 23.3 | 23.4 | 22.5 | 23.2 | 18.8 |
| M-XYL | 19.8 | 19.9 | 53.5 | 51.6 | 54.3 | 53.5 | 53.9 | 53.9 | 54.3 | 51.1 | 51.5 | 41.9 |
| C9+ | 5.3 | 0.8 | 0.5 | 0.4 | 0.5 | 0.4 | 0.5 | 0.5 | 0.4 | 1.1 | 0.8 | 2.0 |
| M-ET | 1.8 | 2.1 | | | | | | | | | | 0.6 |
| P-ET | 1.0 | 1.1 | | | | | | | | | | 0.4 |
| O-ET | 0.5 | 0.6 | | | | | | | | | | 0.1 |
| 1,3,5-TMB | 4.0 | 4.0 | | | | | | | | | | 0.4 |
| 1,2,4-TMB | 10.4 | 10.4 | | | | | | | | | | 1.5 |
| 1,2,3-TMB | 1.6 | 1.6 | | | | | | | | | | 0.2 |
| EB RATE (MOLES/MIN) | 0.00075 | 0.00075 | 0.00452 | 0.00452 | 0.00452 | 0.00452 | 0.00452 | 0.00452 | 0.00075 | 0.00075 | 0.00075 | 0.00075 |
| XYL RATE (MOLES/MIN) | 0.00328 | 0.00328 | 0.01967 | 0.01967 | 0.01967 | 0.01967 | 0.01967 | 0.01967 | 0.00328 | 0.00328 | 0.00328 | 0.00328 |
| H2 RATE (MOLES/MIN) | 0.01652 | 0.01652 | 0.06473 | 0.06473 | 0.06473 | 0.06473 | 0.06473 | 0.06429 | 0.01652 | 0.01696 | 0.01696 | 0.01696 |
| H2/HC MOLAR RATIO | 4.068 | 4.068 | 2.657 | 2.657 | 2.657 | 2.657 | 2.657 | 2.639 | 4.068 | 4.178 | 4.178 | 4.178 |
| LHSV | 2.00 | 2.00 | 12.00 | 12.00 | 12.00 | 12.00 | 12.00 | 12.00 | 2.00 | 2.00 | 2.00 | 2.00 |
| WHSV | 2.78 | 2.78 | 16.70 | 16.70 | 16.70 | 16.70 | 16.70 | 16.70 | 2.78 | 2.78 | 2.78 | 2.78 |
| XYLENE CONVERSION | | | | | | | | | | | | |
| M-XYLENE CONV. | 34.9 | 33.7 | 0.4 | 0.6 | −0.2 | 0.6 | 0.2 | 0.2 | −0.2 | 3.0 | 2.5 | 12.2 |
| O-XYLENE CONV. | 16.1 | 15.5 | 0.6 | 1.3 | 1.4 | 1.1 | 1.5 | 1.5 | 1.4 | 2.3 | 1.6 | 6.0 |
| P-XYLENE PRODUCTION | 5.8 | 6.5 | −2.5 | 0.3 | −2.5 | −1.7 | 0.2 | 0.2 | −2.5 | 3.1 | 2.3 | 12.0 |
| XYLENE CONSUMPTION | | | | | | | | | | | | |
| % XYLENES RECOV. | 45.9 | 46.4 | 97.7 | 97.0 | 97.9 | 98.2 | 100.6 | 100.6 | 97.9 | 99.7 | 100.1 | 94.7 |
| TOLUENE YIELD (WT %) | 27.4 | 28.0 | 0.2 | 0.1 | 0.1 | 0.1 | 0.1 | 0.1 | 0.2 | 0.4 | 0.3 | 2.3 |
| ETHYLBENZENE DISPROPORT. | | | | | | | | | | | | |
| % EB CONSUMED | 90.7 | 87.9 | −11.7 | −2.6 | −13.9 | −12.8 | −2.1 | −2.1 | −13.9 | 0.5 | −0.6 | 13.4 |
| BENZENE YIELD (WT %) | 6.9 | 7.0 | 0.0 | −0.1 | −0.1 | −0.1 | −0.1 | −0.1 | −0.1 | 0.2 | 0.1 | 0.6 |
| HEAVIES YIELD (WT %) | 23.5 | 20.7 | 0.1 | 0.0 | 0.1 | 0.0 | 0.1 | 0.1 | 0.0 | 0.7 | 0.4 | 4.8 |

TABLE VI

| EXPERIMENT | | 8E | | 10 | | 11 | | 12 | 13 |
|---|---|---|---|---|---|---|---|---|---|
| SAMPLE NUMBER | 8D.2 | 8E.1 | 8E.2 | 10.1 | 10.2 | 11.1 | 11.2 | 12.1 | 13.1 |
| AGE OF CATALYST IN DAYS | 4.1 | 7.0 | 8.0 | 9.0 | 10.0 | 10.3 | 10.6 | 11.0 | 12.0 |

TABLE VI-continued

| EXPERIMENT | | 8E | | 10 | | 11 | | 12 | 13 |
|---|---|---|---|---|---|---|---|---|---|
| SAMPLE NUMBER | 8D.2 | 8E.1 | 8E.2 | 10.1 | 10.2 | 11.1 | 11.2 | 12.1 | 13.1 |
| AVG. BATH TEMP. | 354 | 407 | 403 | 392 | 410 | 410 | 410 | 360 | 350 |
| PRESSURE (PSIG) | 600 | 600 | 600 | 300 | 300 | 300 | 300 | 300 | 300 |
| LIQUID ANALYSIS WT % | | | | | | | | | |
| NON-AROM | 0.2 | 0.3 | 0.3 | 0.2 | 0.3 | 0.2 | 0.2 | 0.2 | 0.2 |
| BZ | 0.9 | 3.5 | 3.5 | 2.3 | 2.5 | 1.0 | 0.8 | 0.2 | 0.7 |
| TOL | 3.2 | 14.9 | 15.4 | 9.5 | 10.2 | 3.3 | 2.7 | 0.6 | 2.0 |
| EB | 15.4 | 8.0 | 7.6 | 11.5 | 11.2 | 16.4 | 16.8 | 18.8 | 17.3 |
| P-XYL | 14.7 | 11.7 | 11.6 | 14.0 | 13.7 | 14.8 | 14.6 | 5.8 | 12.9 |
| O-XYL | 18.1 | 11.9 | 11.6 | 14.4 | 14.2 | 18.6 | 19.1 | 22.7 | 19.9 |
| M-XYL | 40.7 | 27.8 | 27.2 | 33.6 | 33.3 | 40.7 | 41.3 | 50.9 | 43.5 |
| C9+ | 2.7 | 5.9 | 6.1 | 4.3 | 4.0 | 1.4 | 1.5 | 0.8 | 1.3 |
| M-ET | 0.8 | 3.0 | 3.2 | 2.0 | 2.1 | 0.7 | 0.6 | | 0.4 |
| P-ET | 0.5 | 1.6 | 1.6 | 1.1 | 1.1 | 0.4 | 0.4 | | 0.3 |
| O-ET | 0.2 | 0.8 | 0.8 | 0.5 | 0.5 | 0.2 | 0.1 | | 0.1 |
| 1,3,5-TMB | 0.5 | 2.7 | 2.8 | 1.6 | 1.7 | 0.4 | 0.3 | | 0.2 |
| 1,2,4-TMB | 1.9 | 6.9 | 7.3 | 4.4 | 4.6 | 1.6 | 1.3 | | 0.9 |
| 1,2,3-TMB | 0.2 | 1.0 | 1.0 | 0.6 | 0.6 | 0.3 | 0.3 | | 0.3 |
| EB RATE (MOLES/MIN) | 0.00075 | 0.00075 | 0.00075 | 0.00075 | 0.00075 | 0.00452 | 0.00452 | 0.00452 | 0.00075 |
| XYL RATE (MOLES/MIN) | 0.00328 | 0.00328 | 0.00328 | 0.00328 | 0.00328 | 0.01967 | 0.01967 | 0.01967 | 0.00328 |
| H2 RATE (MOLES/MIN) | 0.01696 | 0.01696 | 0.01696 | 0.01741 | 0.01696 | 0.06473 | 0.06473 | 0.06473 | 0.01696 |
| H2/HC MOLAR RATIO | 4.178 | 4.178 | 4.178 | 4.288 | 4.178 | 2.657 | 2.657 | 2.657 | 4.178 |
| LHSV | 2.00 | 2.00 | 2.00 | 2.00 | 2.00 | 12.00 | 12.00 | 12.00 | 2.00 |
| WHSV | 2.78 | 2.78 | 2.78 | 2.78 | 2.78 | 16.70 | 16.70 | 16.70 | 2.78 |
| XYLENE CONVERSION | | | | | | | | | |
| M-XYLENE CONV. | 13.4 | 26.3 | 27.1 | 20.5 | 20.9 | 13.4 | 12.8 | 3.2 | 10.6 |
| O-XYLENE CONV. | 6.7 | 12.9 | 13.3 | 10.4 | 10.6 | 6.2 | 5.7 | 2.1 | 4.9 |
| P-XYLENE PRODUCTION | 12.2 | 9.2 | 9.0 | 11.5 | 11.2 | 12.3 | 12.1 | 3.3 | 10.4 |
| XYLENE CONSUMPTION | | | | | | | | | |
| % XYLENES RECOV. | 92.6 | 64.7 | 63.5 | 78.1 | 77.1 | 93.3 | 94.5 | 100.0 | 96.1 |
| TOLUENE YIELD (WT %) | 3.0 | 14.7 | 15.1 | 9.3 | 10.0 | 3.1 | 2.5 | 0.4 | 1.8 |
| ETHYLBENZENE DISPROPORT. | | | | | | | | | |
| % EB CONSUMED | 17.6 | 57.2 | 59.6 | 38.5 | 40.2 | 12.3 | 10.2 | −0.5 | 7.5 |
| BENZENE YIELD (WT %) | 0.8 | 3.4 | 3.7 | 2.2 | 2.4 | 0.9 | 0.7 | 0.1 | 0.6 |
| HEAVIES YIELD (WT %) | 6.4 | 21.5 | 22.3 | 14.1 | 14.2 | 4.6 | 4.1 | 0.4 | 3.1 |

TABLE VII

| | 1 | 2 | 2B | 3 | 4 | 4B | 5 | 6 | 7 | 8 | 8B | 8C | 8D | 8E | 9 | 10 | 11 | 12 | 13 |
|---|---|---|---|---|---|---|---|---|---|---|---|---|---|---|---|---|---|---|---|
| TEMP. C. | 472 | 303 | 351 | 208 | 452 | 401 | 451 | 353 | 468 | 209 | 206 | 307 | 354 | 405 | 205 | 401 | 410 | 360 | 350 |
| PRESS | 600 | 250 | 250 | 200 | 200 | 200 | 200 | 610 | 600 | 600 | 600 | 600 | 600 | 600 | 600 | 300 | 300 | 300 | 300 |
| LSHV | 2.0 | 13.3 | 13.4 | 1.0 | 1.0 | 1.0 | 13.9 | 1.0 | 2.0 | 12.0 | 2.0 | 2.0 | 2.0 | 2.0 | 12.0 | 2.0 | 12.0 | 12.0 | 2.0 |
| WHSV | 2.8 | 18.5 | 18.7 | 1.4 | 1.4 | 1.4 | 19.3 | 1.4 | 2.8 | 9.7 | 2.8 | 2.8 | 2.8 | 2.8 | 16.7 | 2.8 | 16.7 | 16.7 | 2.8 |
| H2/HC | 4.6 | 4.4 | 4.3 | 4.0 | 5.9 | 5.9 | 4.0 | 0.0 | 4.1 | 3.4 | 4.1 | 4.2 | 4.2 | 4.2 | 2.7 | 4.2 | 2.7 | 2.7 | 4.2 |
| NON-AROM | 0.5 | 0.0 | 0.0 | 0.2 | 0.3 | 0.3 | 0.1 | 0.2 | 0.9 | 0.5 | 0.2 | 0.2 | 0.2 | 0.3 | 0.2 | 0.2 | 0.2 | 0.2 | 0.2 |
| BENZENE | 5.8 | 0.1 | 0.1 | 0.0 | 3.7 | 3.4 | 0.4 | 0.1 | 6.8 | 3.4 | 0.0 | 0.3 | 0.8 | 3.5 | 0.0 | 2.4 | 0.9 | 0.2 | 0.7 |
| TOLUENE | 23.7 | 0.1 | 0.1 | 0.2 | 13.8 | 12.8 | 1.0 | 0.2 | 28.0 | 14.2 | 0.4 | 0.6 | 2.9 | 15.1 | 0.3 | 9.8 | 3.0 | 0.6 | 2.0 |
| EB | 3.3 | 18.8 | 18.8 | 18.8 | 8.4 | 9.1 | 18.2 | 18.9 | 2.0 | 11.2 | 21.3 | 18.7 | 15.8 | 7.8 | 19.8 | 11.3 | 16.6 | 18.8 | 17.3 |
| P-XYLENE | 9.5 | 0.0 | 1.8 | 0.0 | 12.2 | 14.1 | 1.0 | 2.8 | 8.7 | 4.8 | 0.0 | 5.2 | 14.6 | 11.6 | 2.1 | 13.8 | 14.7 | 5.8 | 12.9 |
| O-XYLENE | 9.8 | 24.6 | 24.7 | 24.3 | 13.9 | 13.5 | 23.2 | 24.1 | 9.0 | 16.3 | 23.4 | 22.9 | 18.5 | 11.7 | 23.4 | 14.3 | 18.9 | 22.7 | 19.9 |
| M-XYLENE | 21.9 | 56.1 | 54.5 | 56.0 | 30.6 | 29.9 | 54.9 | 53.3 | 19.8 | 36.8 | 54.3 | 51.3 | 41.3 | 27.4 | 53.8 | 33.4 | 41.0 | 50.9 | 43.5 |
| total xyl | 41.2 | 80.7 | 81.0 | 80.3 | 56.6 | 57.5 | 79.2 | 80.2 | 37.5 | 58.0 | 77.7 | 79.4 | 74.4 | 50.7 | 79.2 | 61.5 | 74.6 | 79.4 | 76.3 |
| HEAVIES | 23.8 | 0.2 | 0.0 | 0.4 | 17.1 | 16.9 | 1.2 | 0.4 | 23.3 | 11.9 | 0.4 | 1.0 | 6.0 | 22.3 | 0.5 | 14.5 | 4.8 | 0.8 | 3.5 |
| M-XYL CON | 32.2 | −2.0 | −0.4 | −1.9 | 23.5 | 24.2 | −0.8 | 0.8 | 34.3 | 17.3 | −0.2 | 2.8 | 12.8 | 26.7 | 0.3 | 20.7 | 13.1 | 3.2 | 10.6 |
| O-XYL CON | 15.0 | 0.2 | 0.1 | 0.5 | 10.9 | 11.3 | 1.6 | 0.7 | 15.8 | 8.5 | 1.4 | 1.9 | 6.3 | 13.1 | 1.4 | 10.5 | 6.0 | 2.1 | 4.9 |
| P-XYL PRO | 7.0 | −2.5 | −0.7 | −2.5 | 9.7 | 11.6 | −1.5 | 0.3 | 6.2 | 2.3 | −2.5 | 2.7 | 12.1 | 9.1 | −0.4 | 11.3 | 12.2 | 3.3 | 10.4 |
| % XYL REC | 50.6 | 99.1 | 99.5 | 98.7 | 69.6 | 70.6 | 97.3 | 98.6 | 46.0 | 71.2 | 95.4 | 97.5 | 91.3 | 62.3 | 97.3 | 75.6 | 91.6 | 97.5 | 93.7 |
| TOL YIELD | 23.5 | −0.1 | −0.1 | 0.0 | 13.6 | 12.6 | 0.8 | 0.0 | 27.8 | 14.0 | 0.2 | 0.4 | 2.7 | 14.9 | 0.1 | 9.6 | 2.8 | 0.4 | 1.8 |
| % EB CONS | 82.6 | −0.4 | −0.8 | −0.6 | 55.1 | 51.3 | 2.9 | −0.9 | 89.5 | 40.0 | −13.9 | −0.1 | 15.5 | 58.4 | −5.7 | 39.4 | 11.2 | −0.5 | 7.5 |
| BZ YIELD | 5.7 | 0.0 | 0.0 | −0.1 | 3.6 | 3.3 | 0.3 | 0.0 | 6.7 | 3.3 | −0.1 | 0.2 | 0.7 | 3.4 | −0.1 | 2.3 | 0.8 | 0.1 | 0.6 |
| C9+ YIELD | 23.5 | −0.2 | −0.4 | 0.1 | 16.8 | 16.5 | 0.8 | 0.1 | 22.9 | 11.5 | 0.0 | 0.6 | 5.6 | 21.9 | 0.1 | 14.2 | 4.4 | 0.4 | 3.1 |

The xylene isomerization process of the present invention is temperature and pressure dependent as shown by the experimental work reported in Tables III–VII. In the summary of results set forth in Table VII, substantially no activity of the catalyst for xylene or ethylbenzene disproportionation or xylene isomerization was observed for runs carried out at temperatures ranging from about 200°–300° C. and pressures from 200–600 psig. A similar result was observed in Run 2B which was carried out at 351° C. and 250 psig, with a space velocity of 18.7 WHSV. However, as reflected in Run 13, when the pressure was increased to about 300 psig and the space velocity reduced to 2.8 WHSV, substantial xylene isomerization was achieved but only a small amount of ethylbenzene disproportionation was found to occur. At a slightly higher temperature of 360° with a sixfold increase in space velocity as shown in Run 12, only modest xylene isomerization resulted. When the pressure was increased to 600 psig while retaining the space velocity of 2.8 WHSV (Run 8D), about 20 percent disproportionation of ethylbenzene was observed along with substantial xylene isomerization as indicated by the very high para-xylene content. Similar results were observed in Run 11, when the pressure was decreased by one-half to 300 psig and the temperature increased to 410° C. Based upon the experimental data, this value appears to be the optimum temperature for the xylene isomerization reaction.

At higher temperatures of about 450°–500° C., reasonably good results in terms of ethylbenzene disproportionation and para-xylene yield can be obtained. However, these are achieved at the expense of disproportionation of xylene to toluene and $C_9+$ aromatics as indicated by Run 4. Very substantial losses through xylene disproportionation occur at a higher pressure of 600 psig and temperatures of about 470° C., as reflected in Runs 1 and 7.

Based upon the experimental data reported herein, the isomerization reaction should be carried out at a temperature of at least 350° C. Normally, in order to limit the xylene disproportionation reaction, the temperature within the reaction zone should not exceed 500° C. When the temperature is near this level, the pressure should be relatively low in order to minimize disproportionation of xylene. However, where substantial disproportionation of xylenes is acceptable, temperatures of up to about 600° C. can be employed. The hydrogen pressure (or hydrogen partial pressure where the hydrogen stream is not 100% pure hydrogen) usually should be about 250–600 psig or above, and pressures within the range of about 300–500 psig normally will be preferred in terms of plant design criteria and the impact of pressure upon the loss of xylene content through disproportionation to toluene and $C_9+$ alkylaromatic hydrocarbons. However, plant design limitations will often permit higher pressures of up to about 600 psig. The preferred operating temperature normally will be within the range of 400–440° C. As noted above, higher temperatures normally indicate the use of lower pressures. For example, when the temperature is relatively high, i.e. about 450° C., a relatively low pressure, near 200 psig or slightly above, should be used as indicated by Run 5.

It will be recognized that variations in temperature and pressure, usually small, will exist across the catalyst bed, and the pressures and temperatures given herein are average values. For example, in a typical catalyst bed, there may be a pressure gradient across the bed such that pressure at the outlet is 5–10 psi lower than the pressure at the inlet. Similarly, the temperature across the bed may vary by a small amount, usually no more than 5°–15° C. The outlet temperature typically will be a few degrees higher than the inlet temperature (although the reverse condition may also prevail). In addition, the average temperature of the bed normally will be increased modestly as the catalyst ages and the temperatures set forth herein are those existing in the reaction zone when the catalyst is fresh. For example, where the reaction zone is initially operated at a temperature of 350° C., this may be progressively increased in one or more increments throughout the life of the catalyst (before regeneration) to arrive at a final temperature of about 50°–100° C. higher than the initial temperature. After regeneration of the catalyst, the reaction temperature may then be reduced to its initial value and again progressively increased until the next regeneration step.

Space velocities (based upon the composite amount of ethylbenzene and xylene) may vary from about 0.5–20 WHSV but normally will fall within the range of about 1–10. Preferred space velocities are within the range of 3–7 WHSV.

The hydrogen co-feed, while inert in the isomerization and disproportionation reactions and thus not necessary for the isomerization process, is highly desirable in order to prevent coking of the mordenite catalyst which results in a premature loss of activity. This is evidenced by Run 4 in which the hydrogen co-feed was omitted for a period of about one day, and in Runs 7 & 8 in which hydrogen co-feed was omitted for about one and one-half days. It is believed that omission of the hydrogen co-feed in Run 4 somewhat diminished the activity of the catalyst for the subsequent Runs 5 & 6. In any case, catalytic activity was undoubtedly reduced substantially during Runs 7 & 8. The subsequent runs were not affected since, as noted previously, the catalyst was regenerated after Run 8. In the experimental data, the molar ratio of hydrogen to hydrocarbons (the composite of xylenes and ethylbenzenes in the feed) varied from about 2.7 to 5.9. Hydrogen co-feed above or below the amounts used in the experimental data can be used but hydrogen/hydrocarbon molar ratios of at least 3 are preferred. Ratios of 3 or more can be expected to produce good results in terms of para-xylene yield and ethylbenzene disproportionation and normally the ratio will be within the range of 3–10.

As disclosed in parent application Ser. No. 826,848, a start-up procedure for the mordenite catalyst may employed in which a preflush gas is supplied to the reaction zone prior to initiating the disproportionation reaction. The preflush gas is heated to a temperature sufficient to strip water from the catalyst so that a substantially dehydrated catalyst is arrived at when the hydrocarbon feed is started. A similar start-up procedure may be used in the isomerization process of the present invention. In this embodiment of the invention, hydrogen, nitrogen or another inert gas is employed to precondition the catalyst bed prior to commencing xylene feed in the isomerization process. The preconditioning procedure involves flowing the hot inert gas through the catalyst bed as disclosed in application Ser. No. 826,848.

While this embodiment of the invention is not to be limited by theory, high silica/alumina ratio mordenites of the type employed in the present invention are hygroscopic and it is believed that the presence of water in the catalyst framework blocks some active sites. By passing the hot gas through the catalyst bed before the catalyst is exposed to toluene, the catalyst is dehydrated and more active sites are made available for the conversion reactions.

The duration of the preflush procedure and the temperature of the hot gas are interrelated with the higher temperatures permitting a shorter duration. As a practical matter it will usually be desirable to heat the preflush gas to a temperature of at least 350° C. and to continue the preflush procedure for a period of at least 24 hours. Normally the preflush step will be carried out to the point at which no more water is condensed from the effluent gas and thereafter continued for an additional period of about 12 hours. That is, the preflush gas injection is continued for 12 hours after water condensation stops. Usually the preflush gas will simply be heated to approximately the same temperature as the feed stream during the isomerization reaction. Higher temperatures should be avoided so as to not expose the catalyst to deactivating temperature conditions.

Having described specific embodiments of the present invention, it will be understood that modification thereof may be suggested to those skilled in the art, and it is intended to cover all such modifications as fall within the scope of the appended claims.

We claim:

1. In a process for the isomerization of a xylene feed stock to produce a product having an enhanced para-xylene content, the steps comprising:
   a. passing said xylene feed stock containing meta-xylene into a reaction zone and in contact with a mordenite catalyst having a silica/alumina mole ratio of at least 30,
   b. supplying hydrogen to said reaction zone,
   c. operating said reaction zone at a temperature within the range of 350°-600° C. and a hydrogen pressure within the range of 200-1000 psig to effect isomerization of said xylene feedstock to provide a product of increased para-xylene content reduced meta-xylene content, and
   d. withdrawing said product from said reaction zone.

2. The method of claim 1 wherein said mordenite catalyst has a silica/alumina mole ratio within the range of 40-60.

3. The method of claim 1 wherein said mordenite catalyst has a silica/alumina ratio of about 48.

4. The method of claim 1 wherein said feedstock contains a mixture of xylene isomers.

5. In a process for the isomerization of a xylene feed stock to produce a product having an enhanced para-xylene content and a diminished ethylbenzene content, the steps comprising:
   a. passing said xylene feed stock containing a mixture of xylene isomers and ethylbenzene in which para-xylene is present in less than an equilibrium amount and ethylbenzene is present in a concentration greater than the para-xylene concentration into a reaction zone and in contact with a mordenite catalyst having a silica/alumina mole ratio of at least 30,
   b. supplying hydrogen to said reaction zone,
   c. operating said reaction zone at a temperature within the range of 350°-600° C. and a hydrogen pressure within the range of 200-1000 psig to effect isomerization of xylene isomers to provide an increased para-xylene content and disproportionation of ethylbenzene to provide a reduced ethylbenzene content, and
   d. withdrawing a product of increased para-xylene content and a diminished ethylbenzene content from said reaction zone.

6. The method of claim 5 wherein said mordenite catalyst has a silica/alumina mole ratio within the range of 40-60.

7. The method of claim 5 wherein said mordenite catalyst has a silica/alumina ratio of about 48.

8. The method of claim 5 wherein said feed stream contains ortho-xylene in an amount greater than the para-xylene content of said feed stream and wherein the isomerization product withdrawn from said reaction zone contains a lower ortho-xylene content than said feed stream.

9. The method of claim 5 wherein said reaction zone is operated at a temperature within the range of 350°-500° C.

10. The method of claim 9 wherein said reaction zone is operated at a hydrogen pressure within the range of 200-600 psig.

11. The method of claim 5 wherein said reaction zone is operated at a hydrogen pressure of at least 300 psig.

12. The method of claim 11 wherein said reaction zone is operated at a temperature within the range of 400°-440° C.

13. The method of claim 5 wherein hydrogen is supplied to said reaction zone at a rate to provide a mole ratio of hydrogen to the composite of xylene and ethylbenzene in said feed stream of at least 3.

14. The method of claim 5 wherein said xylene feedstock is supplied to said reaction zone to provide a space velocity over said catalyst within the range of 1-10 WHSV.

15. The method of claim 14 wherein said space velocity is within the range of 3-7 WHSV.

16. The method of claim 5 further comprising the step of prior to supplying said xylene feedstock to said reaction zone, initiating a start-up procedure by supplying a hot preflush gas to said reaction zone and flowing said hot gas into contact with said mordenite catalyst.

17. The method of claim 16 wherein said preflush gas is supplied to said reaction zone at a temperature of at least 350° C. for a period of at least 24 hours.

18. The method of claim 16 wherein said preflush gas comprises hydrogen.

* * * * *